United States Patent [19]

Grinnell

[11] Patent Number: 4,957,902

[45] Date of Patent: Sep. 18, 1990

[54] PEPTIDE INHIBITORS OF WOUND CONTRACTION

[75] Inventor: Frederick Grinnell, Dallas, Tex.

[73] Assignee: Board of Regents, the University of Texas System, Austin, Tex.

[21] Appl. No.: 287,005

[22] Filed: Dec. 20, 1988

[51] Int. Cl.$^5$ .......................... C07K 5/08; C07K 7/06; C07K 5/10

[52] U.S. Cl. ........................................ 514/17; 514/18; 514/16; 530/329; 530/330; 530/350

[58] Field of Search .................... 514/17, 18; 530/350, 530/329, 330

[56] References Cited

U.S. PATENT DOCUMENTS 4,578,079 3/1986 Rouslahti et al. ................... 530/330

OTHER PUBLICATIONS

Yamada et al. (1984) Dualistic Nature of Adhesive Protein Function: Fibronectin and its Biologically Active Peptide Fragments can Autoinhibit Fibronectin Function, The Journal of Cell Biology, vol. 99, Jul. 1984, 29–36.
Pierschbacher et al., "Cell Attachment Activity of Fibronectin can be Duplicated by Small Synthetic Fragments of the Molecule" Nature vol. 309, May 3, 1984, 30–33.
Zitelli, "Seconary Intention Healing: an Alternative to Surgical Repair", Clinics in Dermatology vol. 2, 1984, 92–106.
Telios Pharmaceuticals, Inc. sales brochure.
Peacock, Third Edition, "Wound Repair" Contraction 38–55.
Bell et al., "Production of a Tissue-Like Structure by Contraction of Collagen Lattices by Human Fibroblasts of Different Proliferative Potential in vitro", Proc. Natl. Acad. Sci. U.S.A., vol. 76, No. 3, pp. 1274–1278, Mar. 1979, Cell Biology.
Bellows et al., "Fibroblasts Contracting Three-Dimensional Collagen Gels Exhibit Ultrastructure Consistent with Either Contraction or Protein Secretation" Journal of Ultrastructure Research 78, 178–192 (1982).
Ehrlich et al., "Fibroblast Contraction of Collagen Lattices in vitro: Inhibition by Chronic Inflammatory Cell Mediators" Journal of Cellular Physiology 116:345–351 (1983).
Bellows et al., "Association Between Tension and Orientation of Periodontal Ligament Fibroblasts and Exogenous Collagen Fibres in Collagen Gels in vitro" J. Cell Sci. 58, 125–138 (1982).
Stopak et al., "Connective Tissue Morphogenesis by Fibroblast Traction" Developmental Biology 90, 383–398 (1982).
Grinnell et al., "Reorganization of Hydrated Collagen Lattices by Human Skin Fibroblasts" J. Cell Sci. 66, 51–63 (1984).
Guidry et al., "Studies on the Mechanism of Hydrated Collagen Gel Reorganization by Human Skin Fibroblasts" J. Cell Sci. 79, 67–81 (1985).
Guidry et al., "Heparin Modulates the Organization of Hydrated Collagen Gels and Inhibits Gel Contraction by Fibroblasts" The Journal of Cell Biology, vol. 104, Apr. 1987, 1097–1103.
Dedhar et al., "A Cell Surface Receptor Complex for Collagen Type I Recognizes the Arg-Gly-Asp Sequence" The Journal of Cell Biology, vol. 104, Mar. 1987, 585–593.
Steinberg et al., "Establishment and Transformation Diminish the Ability of Fibroblasts to Contract a Native Collagen Gel" The Journal of Cell Biology, vol. 87, Oct. 1980, 304–308.

(List continued on next page.)

Primary Examiner—Schain Howard E.
Assistant Examiner—Choon P. Koh
Attorney, Agent, or Firm—Arnold, White & Durkee

[57] ABSTRACT

The present invention involves the inhibition of wound contraction by polypeptides having an amino acid sequence which is similar or identical to certain amino acid sequences of type (I) collagen. A variety of peptides are disclosed which are clinically useful as inhibitors of wound contraction.

16 Claims, 3 Drawing Sheets

OTHER PUBLICATIONS

Donaldson et al., "Newt Epidermal Cell Migration Over Collagen and Fibronectin Involves Different Mechanisms" Journal of Cell Science 90, 325–333 (1988).

Bernard et al., "Structure of a cDNA for the Pro 2 Chaim of Human Type I Procollagen, Comparison with Chick cDNA for Pro 2(I) Identifies Structurally Conserved Features of the Protein and the Gene" Biochemistry 1983, 22, 1139–1145.

Grinnell, "Fibronectin Adsorption on Material Surfaces[a]" Annals New York Academy of Sciences, pp. 281–290.

Horwitz et al., "The Cell Substrate Attachment (CSAT) Antigen has Properties of a Receptor for Laminin and Fibronectin" The Journal of Cell Biology, vol. 101, Dec. 1985, 2134–2144.

Hynes, "Integrins: a Family of Cell Surface Receptors" Cell, vol. 48, 549–554, Feb. 27, 1987.

Izzard et al., "Molecular Biology of Cell Motility in vitro" Expl. Biol. Med., vol. 10, pp. 1–22 (Karger, Basel 1985).

Lark, et al., "Close and Focal Contact Adhesions of Fibroblasts to a Fibronectin–Containing Matrix" Federation Proceedings vol. 44, No. 2, Feb. 1985, 394–403.

McKeown–Longo et al., "Interaction of the 70,000–mol–wt Amino–Terminal Fragment of Fibronectin with the Matrix-Assembly Receptor of Fibroblasts" The Journal of Cell Biology, vol. 100, Feb. 1985, 364–374.

Spiegel et al., "Fibrillar Organization of Fibronectin is Expressed Coordinately with Cell Surface Gangliosides in a Bariant Murine Fibroblast" The Journal of Cell Biology, vol. 102, May 1986, 1898–1906.

Grinnell et al., "Cell Adhesion and Phagocytosis Promoted by Monoclonal Antibodies not Directed Against Fibronectin Receptors" Journal of Cell Science 90, 201–214 (1988).

PEPTIDE INHIBITORS OF WOUND CONTRACTION

BACKGROUND OF THE INVENTION contraction is the process which diminishes the size of a full-thickness open wound, and is characterized by the centripetal movement of the whole thickness of surrounding skin. In man, particularly on the extremities and anterior chest wall, contraction may result in significant deformity and loss of function. Because tensions developed during contraction and formation of subcutaneous fibrous tissue may lead to fixed flexion or fixed extension of the joint, avoidance of contraction is particularly important when the wound involves the area over a joint. Thus, wound contraction can be a serious complication of surgery or trauma.

When a full-thickness segment of skin is excised the wound edges immediately retract enlarging the wound. Initially, the wound bed is covered at first with extravasated blood and cell debris. Within 12 to 24 hours the wound bed is invaded by leukocytes, chiefly the polymorphonuclear variety. These are followed by macrophages, whose principal role is to clean up debris preparatory to new tissue formation. Within a few days, capillaries at the base and edges of the wound enlarge and form endothelial buds which rapidly elongate, forming a network of new capillaries in the wound bed. It is these that give healthy granulation tissue a bright red and granular appearance.

Concomitantly with capillary proliferation, fibroblasts invade the wound area, the greatest number usually being seen first at wound margins. Resting fibroblasts are recruited into the wound region where the activated cells proliferate and secrete a new, collagenous matrix that can be seen throughout the wound bed. A subpopulation of wound fibroblasts (often called "myofibroblasts") contain a highly developed actin/myosin cytoskeleton which has been implicated in wound contraction. These elements, associated with mucopolysaccharides and glycoproteins, comprise a wound base over which movement of skin occurs. Five to nine days after the incision, depending on the site, the centripetal movement of the wound margins begins. Thus, fibroblast activities during wound repair and contraction include adhesion, migration, proliferation, matrix synthesis, and contractile force generation.

At the same time the process of epithelization begins. Epithelium provides the barrier to infection and fluid loss. The processes of epithelization and wound contraction are independent; one can occur without the other. Contraction involves movement of the existing dermis at the wound edge, not the formation of new tissue. Usually, wound contraction ceases after epithelization is complete. In some cases, however, e.g. keloids and hypertrophic scars, contraction of the wound bed continues even after complete epithelization has occurred.

The inhibition of wound contraction has been studied. Substances or procedures which interfere with myofibroblast mobilization, migration, adhesion, or multiplication may inhibit wound contraction. For example, high doses of cortisone or related steroids has been shown to delay the development of granulation tissue, depress proliferation of capillaries, suppress fibroblast proliferation, and accordingly, inhibit wound contraction. On the other hand, smaller doses of cortisone have been reported to have no effect on wound contraction. Because steroids given in high doses cause a plurality of untoward effects in patients, steroids are not clinically useful in inhibiting wound contraction.

Cellular poisons, such as cyanide and dinitrophenol, have also been reported to inhibit wound contraction. Likewise, drugs which inhibit smooth muscle contraction have been reported to inhibit wound contraction, for example, colchicine, vinblastine and phenyltoin. These inhibitors of wound contraction (glucocorticosteroids, colchicine, phenyltoin, etc.) have been demonstrated to effective in in vitro wound healing studies, but they have yet to be demonstrated clinically effective.

Physical intervention has also been demonstrated to affect the rate of wound contraction. The influence of dressings on wound contraction seems to be largely mechanical. An adherent dressing, such as untreated gauze, will delay, but not prevent contraction. If a synthetic film such as nylon or cellophane is applied to a wound surface during the lag phase, before active contraction has started, inhibition of contraction will be observed. Likewise, epithelization and fibroblast invasion are prevented.

The effect of skin grafts on contracting wounds has received considerable attention. It has been observed that if a full-thickness skin graft is applied to an excised wound before wound contraction commences, contraction is inhibited. However, significant problems are associated with skin grafting, for example, cost, source of grafting skin, rejection of graft, secondary infection, and all the risks typically associated with any surgical procedure. Accordingly, a new method of inhibiting wound contraction is needed which overcomes the problems associated with the prior art methods.

A method to inhibit wound contraction by using a polypeptide compound offers many advantages over prior methods of treating wound contraction. Among these are: (1) the effective in vivo inhibition of wound contraction in mammals; (2) the prevention of the untoward effects undesired wound contraction in a patient; (3) lower cost treatment of wound contraction; (4) reduced cellular toxicity, and accordingly, a lower incidence of side effects in a patient; (5) a reduced likelihood of secondary infection; and (6) an increased availability of treatment for patients in need thereof.

Fibroblast contraction of collagen gels[1] bears similarities to wound contraction[2,3] and has been used as a model system for studying connective tissue morphogenesis[4,5]. During contraction, cells bind to nearby collagen fibrils and exert mechanical forces that are propagated throughout the three-dimensional gel by the interconnected collagen fibril network[6-9]. The cell receptors and collagen cell-recognition sequences involved in gel contraction have yet to be identified, but recently several receptors of human osteosarcoma cells were described that recognize the arg-gly-asp sequence in type I collagen coated on tissue culture plastic surfaces[10]. As described herein, the peptide gly-arg-gly-glu-ser-pro (GRGESP) inhibits spreading of human fibroblasts inside collagen gels and markedly decreases gel contraction, but this peptide has no effect on cell spreading on collagencoated surfaces. These results suggest that human fibroblasts can interact with different collagen cell recognition sequences depending upon topographical organization of the collagen.

SUMMARY OF THE INVENTION

One aspect of the present invention involves the use of a polypeptide for inhibiting wound contraction in mammals. The preferred polypeptide has the sequence:

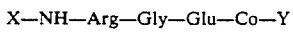

X—NH—Arg—Gly—Glu—Co—Y
  1     2    3 wherein X is a pharmaceutically acceptable N-terminal derivative, or is selected from the group consisting of Z—NH—Val—, Z—NH—Gly—Val—, Z—NH—Ala—, Z—NH—Gly—Ala—, Z—NH—Glu—, Z—NH—Gly—Glu—, Z—NH—Leu—, Z—NH—Gly—Leu—, Z—NH—Asp—, Z—NH—Gly—Asp, Z—NH—Ser—, Z—NH—Gly—Ser—, Z—NH—Pro—, Z—NH—Gly—Pro—, Z—NH—Gln—, Z—NH—Gly—Gln—, —Gly— the term "Z" is a pharmaceutically acceptable N-terminal derivative. The term "Y" is a pharmaceutically acceptable C-terminal derivative and may be selected from the group consisting of —Hyp—CO—R, —Hyp—Gly—CO—R, —Gln—CO—R, —Gln—Gly—CO—R, —Arg—CO—R, —Arg—Gly—CO—R, —Thr—CO—R, —Thr—Gly—CO—R, —Ile—CO—R, —Ile—Gly—CO—R, —Ala—CO—R, —Ala—Gly—CO—R, —Val—CO—R, Val—Ely—CO—R, —Ser—CO—R, —Ser—Pro—CO—R. The term "R" is a pharmaceutically acceptable C-terminal derivative.

In further detail, another aspect of the present invention is a method for inhibiting wound contraction. This method comprises the steps of:

(a) providing a pharmaceutically acceptable composition, including as the active principle a polypeptide as set forth above; and (b) administering a therapeutically effective amount of said pharmaceutically acceptable composition to an individual in need thereof. This administration preferably to the internal or external wound area.

The peptides of the present invention are useful as inhibitors of wound contraction, by themselves or in combination, alone or in appropriate compositions.

DESCRIPTION OF THE PREFERRED EMBODIMENTS

Figure 1:
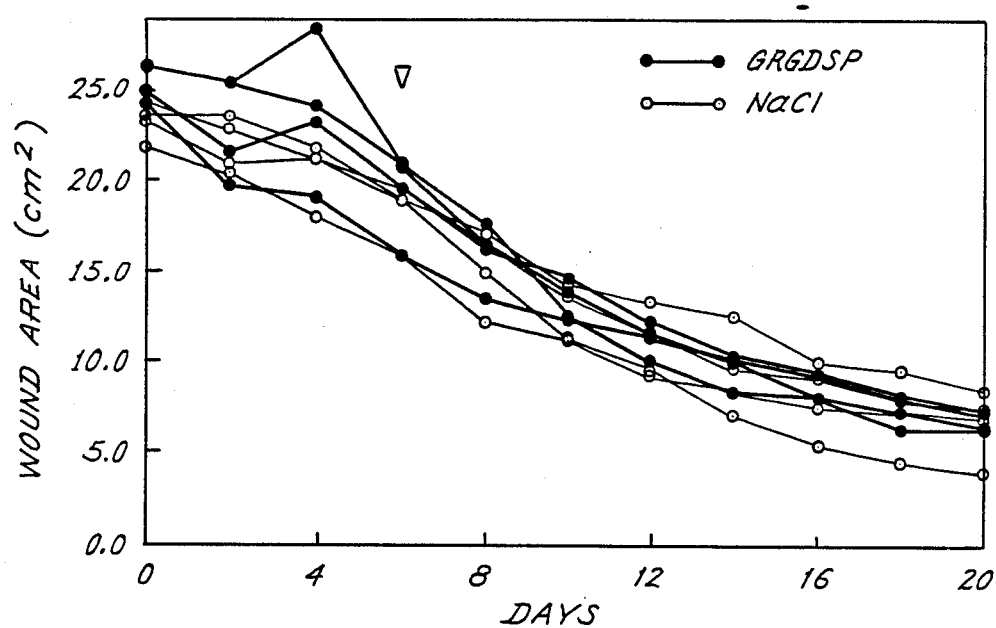
FIG. 1 graphically depicts the time course of guinea pig wound contraction in the presence of NaCl (O) or GRGDSP (●) (gly-arg-gly-asp-ser-pro).

One aspect of the present invention is directed toward use of a polypeptide compound for inhibiting wound contraction in mammals. The polypeptide has the sequence:

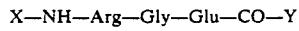

X—NH—Arg—Gly—Glu—CO—Y

The polypeptide of the present invention includes a first amino acid residue (position 1) which is arginine, a second amino acid residue which is glycine (position 2), and at least a third amino acid residue which is glutamic acid (position 3). The first amino acid residue may be either in the D or L configuration, the L- configuration being preferred. The arginine residue at position 1, furthermore, can be in the form of a free amine (i.e., X is hydrogen), or in the form of a first pharmaceutically acceptable N-terminal derivative. The pharmaceutically acceptable N-terminal derivative is derived from the addition (i.e., substitution for X) of any chemical, chemical compound or chemical group at the N-terminal which does not substantially diminish the pharmacological activity or substantially increase the toxicity of the polypeptide compound. Substitutions such as this are well known in the art, for example, alkyl, hydrogen, and acetyl are all groups commonly substituted at the N-terminal in pharmaceutically acceptable preparations of polypeptide compounds.

In another preferred embodiment the arginine residue at position 1, may also be bonded to additional amino acid residues (i.e., X is an amino acid residue). These additional amino acid residues preferably terminate with a pharmaceutically acceptable N-terminal derivative thereof. Among the preferred amino acid residues which may be bound to the arginine of the invention are: Z—NH—Val—, Z—NH—Gly—Val—, Z—NH—Ala—, Z—NH—Gly—Ala—, Z—NH—Glu—, Z—NH—Gly—Glu—, Z—NH—Leu—, Z—NH—Gly—Leu—, Z—NH—Asp—, Z—NH—Gly—Asp—, Z—NH—Ser—, Z—NH—Gly—Ser—, Z—NH—Pro—, Z—NH—Gly—Pro—, Z—NH—Gln—, and Z—NH—Gly—Gln—, where Z is a second pharmaceutically acceptable N-terminal derivative thereof. According to the most preferred embodiment of the present invention, X is Z—NH—Gly—.

The glutamic acid residue at position 3, may be either in the D or L configuration, the L- configuration being preferred. The glutamic acid residue (C-terminal residue) of the sequence, which may be either in the free acid form (i.e., Y is OH), or in the form of another first pharmaceutically C-terminal derivative. The pharmaceutically acceptable C-terminal derivative is derived from the addition (i.e., substitution for Y) of any chemical, chemical compound or chemical group at the C-terminal which does not substantially diminish the pharmacological activity or substantially increase the toxicity of the polypeptide compound. Substitutions such as this are well known and are common in the art. For example, the C-terminal derivative may be in the form of an ester, amide or a pharmaceutically acceptable salt. Among the most preferred pharmaceutically acceptable salts are those of alkaline and alkaline-earth metals such as lithium, sodium, potassium, rubidium, cesium, calcium, magnesium, manganese, barium or other metals such as zinc, copper, etc. Other preferred pharmaceutically acceptable salts include amine cations derived from primary, secondary or tertiary amines.

The glutamic acid C-terminal residue may also be bonded to the N-terminal additional amino acid residues (i.e., Y is an amino acid residue). These additional amino acid residues preferably terminate with a pharmaceutically acceptable C-terminal thereof. Among the preferred amino acid residues of the invention are: —Hyp—CO—R, —Hyp—Gly—CO—R, —Gln—CO—R, —Gln—Gly—CO—R, —Arg—CO—R, —Arg—Gly—CO—R, —Thr—CO—R, —Thr—Gly—CO—R, —Ile—CO—R, —Ile—Gly—CO—R, —Ala—CO—R, —Ala—Gly—CO—R, —Val—CO—R, and —Val—Gly—CO—R, where R is a pharmaceutically acceptable C—terminal derivative. According to the most preferred embodiment of the invention, Y is —Ser—Pro—CO—R, where R is a second pharmaceutically acceptable C-terminal derivative.

The polypeptide compounds of the present invention are preferably three to seven amino acid residues in length; however, these polypeptide compounds may also be incorporated into longer amino acid sequences which inhibits wound contraction. In other words, the sequences corresponding to these polypeptides, when part of a longer peptide, are still part of the present invention, and should be so construed, especially if performing the same function as herein described.

The polypeptides of the present invention may be utilized as inhibitors of wound contraction. These polypeptides, when administered to an individual in need thereof, can be used clinically to inhibit wound contraction during healing. Accordingly, undesirable consequences often associated with wound contraction may be avoided. When used as an inhibitor of wound contraction, the polypeptides are formulated into pharmaceutically acceptable compositions. For example, a pharmaceutically acceptable composition may be dosage forms such as tablets, capsules, powder packets, or liquid solutions, suspensions or elixirs. Sterile liquid formulations such as solutions or suspensions can be prepared for parental use.

Administration may be by any means that facilitates the wound-inhibiting effects of the polypeptides. In the absence of complete epithelization, these polypeptide compounds may be administered but is most preferably topically. In the presence of complete epithelization, these polypeptide compounds may be administered interdermally or subcutaneously, which may be viewed as an internal topical administration. The therapeutically effective amount administered to a patient in need thereof will depend upon the age, health and weight of the recipient, kind of concurrent treatment if any, frequency of treatment, and nature of the effect desired. The peptides of the present invention can be prepared by methods well known in the art of biogenic or chemical polypeptide synthesis or by excision from larger natural proteins. When a pharmaceutically acceptable solution of the polypeptide is topically applied, the polypeptide is preferably at a level between about 0.1 mg/ml and about 1.0 mg/ml.

Having now generally described the invention, the same will become better understood by reference to certain specific examples, which are including for the purpose of explanation only and are not intended to be limiting unless otherwise specified.

EXAMPLE 1

Effect Of The Peptides
Gly—Arg—Gly—Asp—Ser—Pro and
Gly—Arg—Gly—Glu—Ser—Pro On Contraction Of
Guinea Pig Full Thickness Wounds The basic mechanism of wound contraction is the same in lower animals and human beings. Male guinea pigs, less than about 6 months old and weighing from 600 to 700 gm were anesthetized with metaphane. Full-thickness incisional wounds down to the panniculus carnosus muscle, approximately 4×4 cm2, were prepared over the right thoracic wall. The wounds were dressed with petroleum jelly impregnated fine mesh gauze bandages. The dressings were changed every two days. The size of the wounds was recorded by tracing the wound margin outlines on clear acetate sheets each time the dressings were changed. Wound size was measured by image analysis of the tracings with a Zidas digitizing tablet.

Two in vivo experiments were performed, each lasting approximately 1 month. In each experiment 8 animals were divided into two treatment groups. Beginning on day 6, before each re-dressing, one treatment group had its wounds treated with 0.35 ml of isotonic saline, and the other treatment group was treated with 0.35 ml of isotonic saline containing 1 mg/ml of a polypeptide compound. Additional treatments were performed on days 8, 10, 12 and 14.

In the first experiment, the first treatment group was treated with saline alone and the second treatment group was treated with saline containing the polypeptide compound Gly—Arg—Gly—Asp—Ser—Pro (GRGDSP).

In the second experiment, the first treatment group was treated with saline alone and the second treatment group was treated with saline containing the polypeptide compound Gly—Arg—Gly—Glu—Ser—Pro (GRGESP).

In the first experiment there was no significant difference in the time course of contraction for the animals in either treatment group. Each animal is shown as a separate line.

Figure 2:
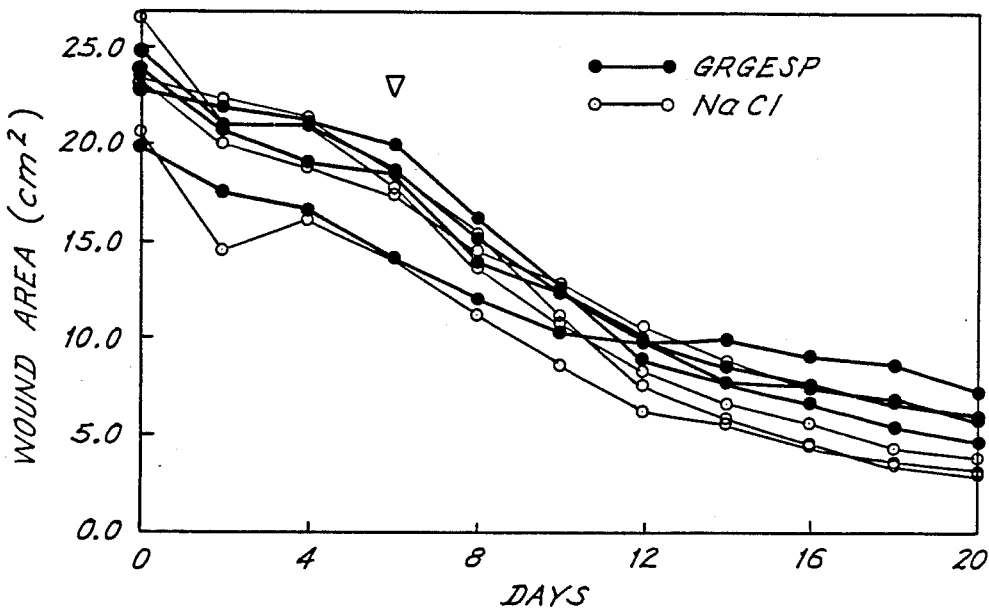
FIG. 2 graphically depicts the time course of guinea pig wound contraction in the presence of NaCl (O) or GRGESP (gly-arg-gly-glu-ser-pro ) (●).
Figure 3:
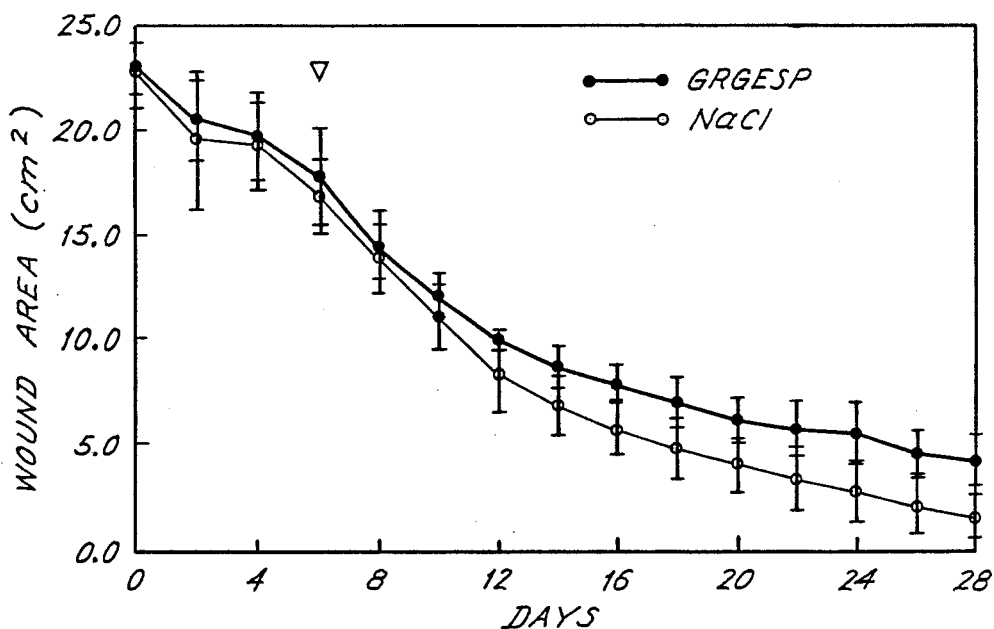
FIG. 3 graphically depicts the averaged time course of guinea pig wound contraction in the presence of NaCl (O) or GRGESP (gly-arg-gly-glu-ser-pro) (●) over a 28 day period.

In the second experiment, there was a marked trend beginning around day 8-10, showing that, the contraction rate of the group given the polypeptide Gly—Arg—Gly—Glu—Ser—Pro (GRGESP) was slower than the contraction rate of the control group. FIG. 2 shows the wound contraction extent for individual animals. Using averages for each group of animals, the extents of contraction were monitored out to 28 days. FIG. 3 shows these results and clearly illustrates a marked inhibition of wound contraction by GRGESP.

The trend towards inhibition of wound contraction shown in FIGS. 2 and 3 was even more significant considering that the treatments were initiated 6 days after contraction had started and that the amount of the polypeptide compound used was low, i.e., 1 mg/ml.

EXAMPLE 2

The Effect Of The Polypeptides
Gly—Arg—Gly—Asp—Ser—Pro and
Gly—Arg—Gly—Glu—Ser—Pro On The Contraction
Of Attached Collagen Gels Human skin fibroblast monolayer cultures were established from foreskins obtained at circumcisions. Hydrated collagen gels were prepared from Vitrogen "100" collagen (Collagen Corp., Palo Alto, Calif.). Fibroblasts were added to neutralized collagen solutions at a concentration of $10^5$ cells/0.2 ml. Aliquots (0.2 ml) of the cell/collagen mixtures were placed in Costar 24 well culture plates. Each aliquot occupied an area outlined by a 12 mm diameter circular score within the well. Gels were polymerized by raising the temperature to 37° and incubating the samples for 60 minutes, after which 1.0 ml of culture medium (DMEM supplemented with 10% FBS and 50 ug/ml ascorbic acid) was added to each well. Medium was changed after 3 days. Radiolabeled collagen gels were prepared from collagen that was acetylated with $^3$H-acetic anhydride (2.5 mCi, 50 mCi/mmole, New England Nuclear Corp).

Fibroblasts were incorporated into collagen gels, and gel contraction was analyzed by measuring decrease in gel thickness. Since the gels were attached to underlying culture dish surfaces, contraction resulted in a decrease in thickness with no change in gel diameter[6,7].

Figure 4:
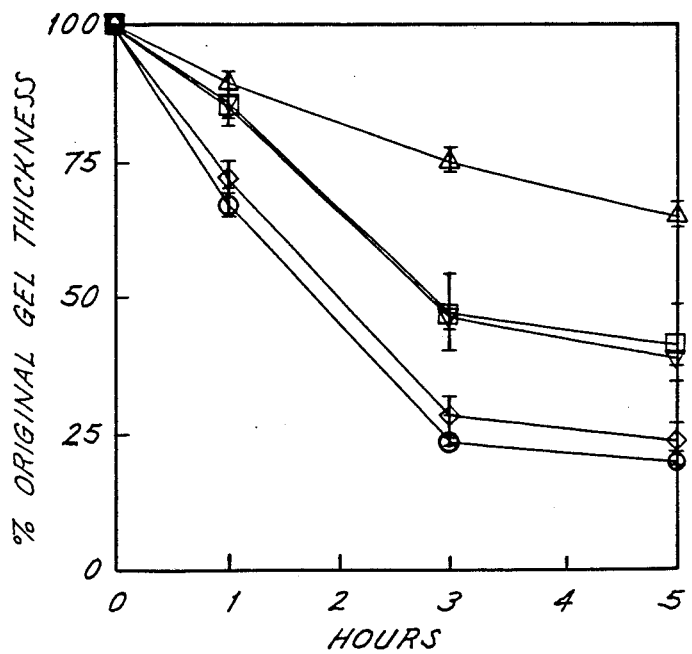
FIG. 4 shows the time course of collagen gel contraction as affected by: 0.50 mg GRGESP/ml (△); 0.25 mg GRGESP/ml (□); 0.50 mg GRGDSP/ml (▽); 0.25 mg GRGDSP/ml (◇) and no peptide (O).

The data shown in FIG. 4 was obtained as follows: The incubations contained peptides as indicated and gel contraction was measured at the times shown. Method: Human skin fibroblasts were added to neutralized collagen solutions (1.5 mg/ml Vitrogen 100 collagen; 95% type I; 5% type III) at a concentration of $10^5$ cells/0.2 ml. Aliquots (0.2 ml) of the cell/collagen mixture were warmed to 22° C., placed in Costar 24 well culture plates, polymerized at 37° C. for 1 hr, and covered with 1 ml of Dulbecco's modified Eagle's medium (DMEM) supplemented with 10% fetal bovine serum. Peptides were added to both the gels and medium. The extent of contraction was determined by measuring gel thickness microscopically using a Zeiss Invertoscope D equipped with a Mitutoyo dial test indicator (0.01-10 mm). See references 7-9 for full details. Under control conditions (no peptide), the rate of contraction was about 25% per hour up to 3 hours (FIG. 4). Addition of the peptide GRGESP to the incubations at a concentration of 0.50 mg/ml reduced contraction to about 8% per hour, i.e. 70% inhibition. With 0.25 mg/ml GRGESP, inhibition was less pronounced, and the rate of contraction was about 18% per hour. Addition of the peptide GRGDSP to the incubations at a concentration of 0.50 mg/ml also resulted in an inhibition of contraction although the effect was much pronounced than observed with GRGESP, and 0.25 mg/ml GRGDSP had no effect on contraction. Essentially the same results were found using commercial peptides from two different sources: Peninsula Laboratories, Inc. (Belmont, Calif.) and Telios Pharmaceuticals, Inc. (San Diego, Calif.).

Microscopic observations showed that fibroblasts inside collagen gels were elongated cells with prominent pseudopodia. In the presence of 0.5 mg/ml GRGESP, however, cells did not extend pseudopodia and most remained round as if they were unable to attach to the collagen. Since collagen gel contraction requires that fibroblasts bind to and mechanically rearrange collagen fibrils within the gels[6,7], inhibition of collagen gel contraction by GRGESP could be explained by the ability of this peptide to inhibit fibroblast binding to collagen. In the presence of 0.5 mg/ml GRGDSP, on the other hand, most of the cells were elongated with pseudopodia similar to control cells, although some cells were only partially spread with round cell bodies.

The above experiments were performed with 10% fetal bovine serum added to the medium because serum is required for collagen gel contraction[7,11]. Experiments also were done in serum-free medium, and we found that after 5 hours the cells were spread in control gels or in gels with GRGDSP. In the presence of GRGESP, however, the cells remained round. Therefore, the inhibition of cell spreading in collagen gels caused by GRGESP was not a consequence of adding serum to the incubation medium.

There are at least two possible interpretations of this observation that GRGESP inhibited gel contraction and cell spreading in collagen gels. One possibility was that human fibroblasts, unlike human osteosarcoma cells[10], recognized the RGE sequence in collagen. For instance, new epidermal cells were shown to recognize both the RGD and RGE sequences in collagen coated on surfaces[12]. Another possibility was that fibroblasts recognized different collagen sequences depending upon the three dimensional organization of collagen. To distinguish between these possibilities, human fibroblast spreading was measured on collagen-coated surfaces in serum-free medium with and without peptides.

Figure 5:
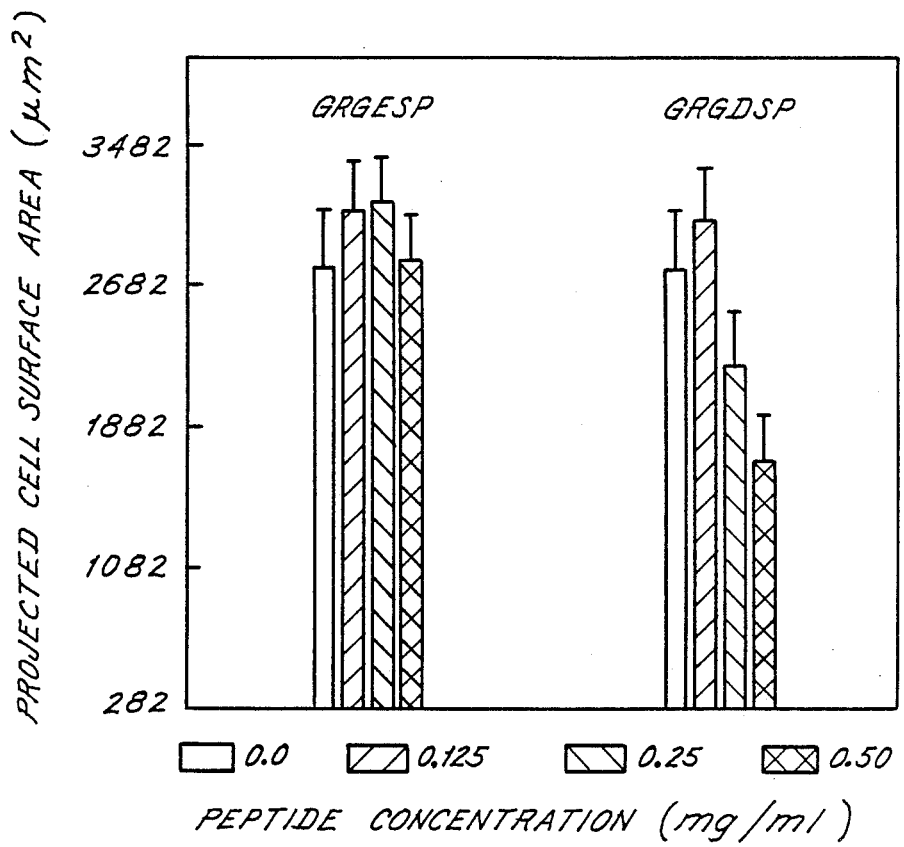
FIG. 5 shows the quantitation of cell spreading on collagen-coated surfaces as affected by GRGESP or GRGDSP at 0.50 mg/ml ⌧; 0.25 mg/ml ⟋⟋; 0.125 mg/ml ⟋⟋ or none ☐.

The incubations contained peptides at the concentrations indicated and cell spreading was measured after 60 minute Method: Falcon 35 mm tissue culture dishes were coated with collagen (Vitrogen 100; 50 ug/ml in DMEM) for 15 minutes at 37° C. and counter-coated for 15 minutes with 1 mg/ml heat denatured bovine serum albumin. Human skin fibroblasts in DMEM with peptides added at the concentrations indicated were incubated on the substrata for 60 minutes at 37°. The end of the incubations, the cells were fixed and projected cell surface areas were measured by superimposing the microscopic field on the digitizing tablet of a Zidas image analyzer. Data presented are averages±95% confidence limits based on measurement of 50-100 cells. See reference 21 for complete details. Addition of 0.5 mg/ml GRGESP had no effect on the extent of fibroblast spreading as measured by projected cell surface area (FIG. 5), although there was a change in the shape of spread cells. In marked contrast, GRGDSP inhibited cell spreading in a dose-dependent fashion, and inhibition amounted to about 50% with 0.5 mg/ml peptide (FIG. 5).

These results show that the peptide GRGESP inhibited gel contraction and cell spreading in collagen gels, but did not inhibit cell spreading on collagen-coated surfaces. Therefore, the effects of GRGESP appear to depend on the topography of the collagen. Collagen molecules have been shown to contain both RGD and RGE sequences[13,14]. In each type I collagen molecule there are 8 RGD sequences (2 in each $\alpha 1(I)$ chain and 4 in the $\alpha 2(I)$ chain) and 22 RGE sequences (9 in each $\alpha 1(I)$ chain and 4 in the $\alpha 2(I)$ chain.

In context, with two preceding and two following amino acids, these sequences include: Gly—Val—Arg—Gly—Glu—Hyp—Gly; Gly—Ala—Arg—Gly—Glu—Hyp—Gly; Gly—Glu—Arg—Gly—Glu—GlnGly; Gly—Ala—Arg—Gly—Glu—Arg—Gly; Gly—Asp—Arg—Gly—Glu—HypGlu; Gly—Pro—Arg—Gly—Glu—Thr—Gly; Gly—Gln—Arg—Gly—Glu—ArgGly; Gly—Asp—Arg—Gly—Glu—Thr—Gly; Gly—Asp—Arg—Gly—Glu—ThrGly; Gly—Glu—Arg—Gly—Glu—Val—Gly; Gly—Glu—Arg—Gly—Glu—IleGly; Gly—Asp—Arg—Gly—Glu—Ala—Gly; and Gly—Ser—Arg—Gly—Glu—Arg—Gly. This spectrum of amino acid settings for the Arg—Gly—Glu component of the present invention is indicative of the scope of peptides likely to have biological activity by mimicking binding cites of collagen containing the Arg—Gly—Glu sequence. While other settings may be appropriate for the Arg—Gly—Glu sequence and may well be useful to inhibit collagen contraction or wound contraction, it is believed that the settings described above include at least many of the most likely successful peptidacious components for this purpose. Although other possibilities cannot be excluded, the simplest interpretation of results is that GRGESP inhibits directly by competing with RGE sequences of collagen that are recognized by fibroblasts when collagen is organized in a three dimensional gel, but are unimportant for fibroblast recognition when collagen is organized as a two dimensional, adsorbed protein layer.

The above interpretation is consistent with several other known features of the binding interactions between cells and adhesion molecules. For instance, molecular orientation of fibronectin molecules coated on different types of plastic surfaces determines how well cells are able to interact with fibronectin[15]. Moreover, different portions of the fibronectin molecule are recognized by separate cell surface receptors that participate in different functions, e.g., cell binding[16,17], focal adhesion formation[18,19], and matrix assembly[20,21]. Therefore, the ability of fibroblasts to recognize different sequences in collagen molecules according to collagen topography may involve separate receptors with unique functions. Such a mechanism would provide cells with the versatility to respond differently to their extracellular matrix not only according to the chemistry of the matrix, but also, according to the three dimensional organization of the matrix.

The citations in the following list are incorporated by reference herein for the reasons cited.

REFERENCES

1 Bell, E., Ivarsson, B. & Merrill, C. *Proc. Natl. Acad. Sci. USA* 76, 1274-1278 (1979).

2. Bellows, C. G., Melcher, A. H., Bhargava, U. & Aubin, J. E. *J. Ultrastruct. Res.* 78, 178-192 (1982).

3. Ehrlich, H. P. & Wyler, D. J. *J. Cell Physiol.* 116, 345-351 (1983).

4. Bellows, C. G., Melcher, A. H. & Aubin, J. E. *J. Cell Sci.* 58, 125-138 (1982).

5. Stopak, D. & Harris, Al K. *Dev. Biol.* 90, 383-398 (1982).

6. Grinnell, F. & Lamke, F. R. *J. Cell Sci.* 66, 51-63 (1984).

7. Guidry, C. & Grinnell, F. *J. Cell Sci.* 79, 67-81 (1985).

8. Guidry, C. & Grinnell, F. *Col. Rel. Res.* 6, 515-529 (1986).

9. Guidry, C. & Grinnell, F. *J. Cell Biol.* 104, 1097-1103 (1987).

10. Dedhar, S., Ruoslahti, E. & Pierschbacher, M. D. *J. Cell Biol.* 104, 585-593 (1987).

11. Steinberg, B. M., Smith, K., Colozzo, M., Pollack, R. *J. Cell Biol.* 87, 304-308.

12. Donaldson, D. J., Mahan, J. T. & Smith Jr., G. N. *J. Cell Sci.* 90, 325-333 (1988).

13. Bernard, M. P., Myers, J. C., Chu, M. L., Ramirez, F., Eikenberry, E. F. & Prockop, D. *J. Biochemistry* (USA) 22, 1139-1145 (1983).

14. Miller, E. J. *Extracellular Matrix Biochemistry* (ed. K. A. Piez A. H. Reddi) Elsevier Science Pub. Co. New York, 41-81 (1984).

5. Grinnell, F. *Ann. N. Y. Acad. Sci.* 516, 280-290 (1987).

16. Horowitz, A., Duggan, K., Greggs, R., Decker, C. & Buck, C. *J. Cell Biol.* 101, 2134-2144 (1985).

17. Hynes, R. O. *Cell* 48, 549-554 (1987).

18. Izzard, C. S., Izzard, S. L. & Depasquale, J. A. *Exp. Biol. Med.* 10, 1-22 (1985).

19. Lark, M. W., Laterra, J. & Culp, L. A. *Fed. Proc.* 44, 4-403 (1985).

20. McKeown-Longo, P. J. & Mosher, D. F. *J. Cell Biol.* 100, 364-374 (1985).

21. Spiegel, S., Yamada, K. M., Hom, B. E., Moss, J. & Fishman, p. H. *J. Cell Biol.* 102, 1898-1906 (1986).

22. Grinnell, F., Ho, Chin-Han & Tuan, Tai-Lan. *J. Cell Sci.* 90, 201-214 (1988).

Changes may be made in the peptides described herein or in the steps or the sequence of steps of the method described herein without departing from the concept and scope of the invention as defined in the following claims.

What is claimed is:

1. A method for inhibiting wound contraction in an individual having a wound, the method comprising the steps of:

providing a pharmaceutically acceptable composition including, as the active principle, a polypeptide compound having the sequence:

wherein X is a pharmaceutically acceptable N terminal derivative, or is selected from the group consisting of Z—NH—Val, Z—NH—Gly—Val, Z—NH—Ala, Z—NH—Gly—Ala, Z—NH—Glu, Z—NH—Gly—Glu, Z—NH—Leu, Z—NH—Gly—Leu, Z—NH—Asp, Z—NH—Gly—Asp, Z—NH—Ser, Z—NH—Gly—Ser, Z—NH—Pro, Z—NH—Gly—Pro, Z—NH—Gln, Z—NH—Gly—Gln, and Z—NH—Gly, where Z is a pharmaceutically acceptable N-terminal derivative thereof, wherein Y is a pharmaceutically acceptable C—terminal derivative, or is selected from the group consisting of —Hyp—CO—R, —Hyp—Gly—CO—R, —Gln—CO—R, —Gln—Gly—CO—R, —Arg—CO—R, —Arg—Gly—CO—R, —Thr—CO—R, —Thr—Gly—CO—R, —Ile—CO—R, —Ile—Gly—CO—R, —Ala—CO—R, —Ala—Gly—CO—R, —Val—CO—R, —Val—Gly—CO—R, —Ser—CO—R, and —Ser—Pro—CO—R, where R is a pharmaceutically acceptable C terminal derivative thereof; and administering said pharmaceutically acceptable composition to an individual so that a wound being treated is exposed to a therapeutically effective amount thereof.

2. The method of claim 1 wherein the polypeptide has the formula:

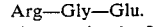

3. The method of claim 1 wherein the polypeptide has the formula:

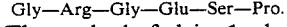

4. The method of claim 1 wherein the polypeptide is incorporated into a longer amino acid sequence.

5. The method of claim 1 wherein the providing step involves biogenic synthesis, chemical synthesis or excision from a polypeptide or protein.

6. A method for inhibiting contraction of a wound, the method comprising: applying to the wound a pharmaceutically acceptable solution comprising a therapeutically effective level of a polypeptide compound having the sequence:

X—NH—Arg—Gly—Glu—CO—Y 1 2 3 wherein X is a first pharmaceutically acceptable N-terminal derivative, or is selected from the group consisting of Z—NH—Val, Z—NH—Gly—Val, Z—NH—Ala, Z—NH—GlyAla, Z—NH—Glu, Z—NH—Gly—Glu, Z—NH—Leu, Z—NH—Gly—Leu, Z—NHAsp, Z—NH—Gly—Asp, Z—NH—Ser, Z—NH—Gly—Ser, Z—NH—Pro, Z—NH—Gly—Pro, Z—NH—Gln, Z—NH—Gly—Gln, and Z—NH—Gly, where Z is a second pharmaceutically acceptable N-terminal derivative;

wherein Y is a first pharmaceutically acceptable C-terminal derivative, or is selected from the group consisting of —Hyp—CO—R; —Hyp—Gly—CO—R, —Gln—CO—R, —Gln—Gly—CO—R, —Arg—CO—R, —Arg—Gly—CO—R, —Thr—CO—R, —Thr—Gly—CO—R, —Ile—CO—R, —Ile—Gly—CO—R, —Ala—CO—R, —Ala—Gly—CO—R, —Val—CO—R, —Val—Gly—CO—R, —Ser—CO—R, and —Ser—Pro—Co—R, where R is a second pharmaceutically acceptable C terminal derivative.

7. The method of claim 6 wherein the therapeutically effective level is between about 0.1 mg/ml and about 1 mg/ml.

8. The method of claim 6 wherein the polypeptide has the formula:

Arg—Gly—Glu.

9. The method of claim 6 wherein the polypeptide has the formula:

Gly—Arg—Gly—Glu—Ser—Pro.

10. The method of claim 6 wherein the polypeptide is incorporated into a longer amino acid sequence.

11. The method of claim 6 wherein the polypeptide is produced by a method involving biogenic synthesis, chemical synthesis or excision from a polypeptide or protein.

12. The method of claim 6 wherein X is hydrogen, alkyl, or acetyl.

13. The method of claim 6 wherein Y is OH, an ester, an amide or a salt.

14. The method of claim 6 wherein Z is hydrogen, alkyl, or acetyl.

15. The method of claim 6 wherein R is OH, an ester, an amide or a salt.

16. The method of claim 1 or 6 wherein the administration is topical, subcutaneous or intramuscular.

* * * * *

UNITED STATES PATENT AND TRADEMARK OFFICE
CERTIFICATE OF CORRECTION

PATENT NO. : 4,957,902
DATED : September 18, 1990
INVENTOR(S) : Frederick Grinnell, Dallas, Tex.

It is certified that error appears in the above—identified patent and that said Letters Patent is hereby corrected as shown below:

In Claim 1, column 10, lines 20-22 delete the term "X-NH-Arg-Gly-Glu-CO-Y

123" and insert the term
--X-NH-Arg-Gly-Glu-CO-Y 1    2   3-- therefor.

In Claim 6, column 11, lines 2-4 delete the term "X-NH-Arg-Gly-Glu-Co-Y

123" and insert the term
--X-NH-Arg-Gly-Glu-CO-Y 1    2   3-- therefor.

In claim 6, column 11, line 8 delete the term "GlyAla," and substitute the term --Gly-Ala,-- therefor.

UNITED STATES PATENT AND TRADEMARK OFFICE
CERTIFICATE OF CORRECTION

PATENT NO. : 4,957,902

DATED : September 18, 1990

INVENTOR(S) : Frederick Grinnell, dallas, Tex.

It is certified that error appears in the above-identified patent and that said Letters Patent is hereby corrected as shown below:

In claim 6, column 11, line 10 delete the term "NHAsp" and substitute the term --NH-Asp-- therefor.

Signed and Sealed this

Twenty-third Day of June, 1992

Attest:

DOUGLAS B. COMER

*Attesting Officer*    *Acting Commissioner of Patents and Trademarks*

UNITED STATES PATENT AND TRADEMARK OFFICE
CERTIFICATE OF CORRECTION

PATENT NO.   :   4,957,902

DATED        :   September 18, 1990

INVENTOR(S)  :   Frederick Grinnell

It is certified that error appears in the above-identified patent and that said Letters Patent is hereby corrected as shown below:

In column 1, line 4, insert the sentence --The United States government may have certain rights in this invention because research relating to the invention was partially supported by National Institutes of Health, Grant No. GM 31321.--

Signed and Sealed this

First Day of December, 1992

Attest:

DOUGLAS B. COMER

*Attesting Officer*   Acting Commissioner of Patents and Trademarks